United States Patent [19]

Immel et al.

[11] 4,233,247
[45] Nov. 11, 1980

[54] PROCESS FOR THE PREPARATION OF 2,2-DIMETHYLOLALKANALS

[75] Inventors: Otto Immel; Hans-Helmut Schwarz, both of Krefeld, Fed. Rep. of Germany

[73] Assignee: Bayer Aktiengesellschaft, Leverkusen, Fed. Rep. of Germany

[21] Appl. No.: 886,218

[22] Filed: Mar. 13, 1978

[30] Foreign Application Priority Data

Apr. 1, 1977 [DE] Fed. Rep. of Germany ....... 2714516

[51] Int. Cl.³ .............................................. C07C 47/26
[52] U.S. Cl. ................................... 568/464; 568/460; 568/461; 568/497
[58] Field of Search ........................................ 260/602

[56] References Cited

U.S. PATENT DOCUMENTS

| | | | |
|---|---|---|---|
| 2,696,477 | 12/1954 | Gagarine et al. | 260/602 |
| 2,863,878 | 12/1958 | Lynn | 260/602 |
| 3,518,310 | 1/1970 | Lutz | 260/602 |

FOREIGN PATENT DOCUMENTS 2507461 9/1976 Fed. Rep. of Germany.
1215269 9/1970 United Kingdom.

Primary Examiner—Werren B. Lone
Attorney, Agent, or Firm—Sprung, Felfe, Horn, Lynch & Kramer

[57] ABSTRACT

An improvement in a process for the preparation of 2,2-dimethylolkanal of the formula

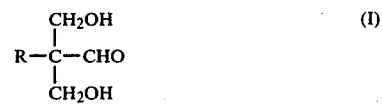

where R denotes an optionally substituted aliphatic radical by reacting 2-alkylacrylaldehyde with formaldehyde in presence of water and a base, the improvement residing in employing an aldehyde of the formula

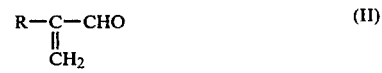

wherein R has the meaning indicated above and a mol ratio of the same to formaldehyde of 1:8–30 at a temperature in the range from −10 to 100° C.

11 Claims, No Drawings

PROCESS FOR THE PREPARATION OF 2,2-DIMETHYLOLALKANALS

The invention relates to a process for the preparation of 2,2-dimethylolalkanals by the reaction of 2-alkylacrylaldehydes in the presence of bases.

It is known, from GB-PS No. 1 215 269, to prepare trimethylolethane by reacting substantially equimolar amounts of 2-methacrylaldehyde with formaldehyde in an aqueous-alkaline medium. The reaction can be represented by the following equation:

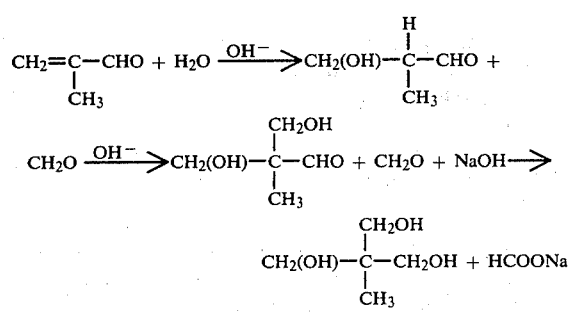

2,2-Dimethylolethanal is probably formed here as an intermediate product, and reacts with formaldehyde and the base by a Cannizzaro reaction to give trimethylolethane and a formate. A similar reaction mechanism can be assumed for the formation of trimethylolpropane from 2-ethylacrylaldehyde and formaldehyde.

Thus, at least stoichiometric amounts of sodium formate are unavoidably obtained as a by-product in the industrial preparation of trimethylolpropane or trimethylolethane. The sodium formate can indeed also be put to an appropriate use, but the demand for sodium formate is not necessarily as great as that for trimethylolpropane. The sodium formate unavoidably obtained thus results in considerable problems of disposal and of environmental protection, which could hitherto be solved in an economical manner only through dumping.

Furthermore, it is known from DT-OS (German Published Specification) No. 2,507,461 (compare Example 5), that 2-alkylacrylaldehydes can be reacted in an aqueous medium with an almost stoichiometric amount of formaldehyde in the presence of specially chosen tertiary aliphatic amines, in which one alkyl radical is highly branched, to give 2,2-dimethylolalkanals. However, the synthesis path indicated in DT-OS (German Published Specification) No. 2,507,461 proceeds only with low yields (compare Example 5 of DT-OS No. (German Published Specification) No. 2,507,461).

A process has now been found for the production of a 2,2-dimethylolalkanal of the general formula

in which R denotes an optionally substituted aliphatic radical, comprising reacting an aldehyde of the general formula $$R-\underset{\underset{CH_2}{\|}}{C}-CHO \quad (II)$$

in which R has the meaning indicated above, with formaldehyde in a molar ratio of 1:8 to 1:30 at temperatures in the range from −10° C. to 100° C., and in the presence of one or more bases and water.

Possible aliphatic radicals (R) are optionally substituted, straight-chain or branched alkyl radicals with up to 15, in particular up to 6, carbon atoms; possible substituents of these radicals are groups which are inert under the reaction conditions, in particular alkoxy groups with 1 to 4 carbon atoms in each case, for example methoxy, ethoxy, propoxy and butoxy. Examples of alkyl radicals which may be mentioned are methyl, ethyl, n-propyl, isopropyl, n-butyl, iso-butyl, n-pentyl, n-hexyl, iso-heptyl, dodecyl and pentadecyl. Preferred optionally substituted alkyl radicals are methyl, ethyl, n-propyl and iso-propyl.

Examples of aldehydes of the formula (II) which may be mentioned are: 2-methylacrylaldehyde and 2-ethyl-, 2-propyl-, 2-butyl-, 2-pentyl- and 2-hexyl-acrylaldehyde. 2-Methylacrylaldehyde, 2-ethylacrylaldehyde, 2-propylacrylaldehyde and 2-butylacrylaldehyde are preferably used in the process according to the invention.

The process according to the invention may be illustrated by the following equation, using 2-methylacrylaldehyde as an example:

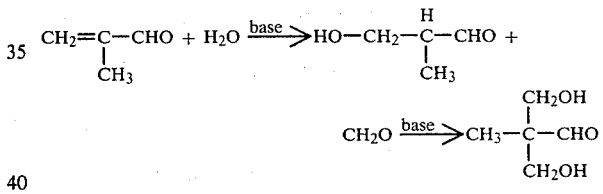

By the process according to the invention, the acrylaldehyde of the formula (II) can be reacted with formaldehyde in a molar ratio of about 1:8 to 1:30, preferably in a molar ratio of 1:10 to 1:20, in the presence of bases at temperatures in the range from about −10° C. to 100° C.

In general, formaldehyde is used as an aqueous solution, preferably with a formaldehyde content of 20 to 40% by weight. Bases which can be used are the bases which are known and customarily used for the aldol condensation.

Examples of bases which may be mentioned are the hydroxides and carbonates of alkali metals and the hydroxides of alkaline earth metals, tertiary amines and basic ion exchangers. The bases can be used both individually and also in mixtures with one another.

Examples which may be mentioned of hydroxides and carbonates of alkali metals and of hydroxides of alkaline earth metals are sodium hydroxide, potassium hydroxide, calcium hydroxide, barium hydroxide, sodium carbonate and potassium carbonate.

Tertiary amines which can be used are heterocyclic, aliphatic and cycloaliphatic amines with up to 20 carbon atoms, preferably up to 15 carbon atoms, aliphatic tertiary amines preferably being employed. The following tertiary amines may be mentioned as examples: trimethylamine, tri-n-propylamine, triethylenediamine, tri-isopropylamine, tri-n-butylamine, triisobutylamine and tri-tert.-butylamine, and also unsymmetric trialkylamines, such as methyldiisopropylamine or dimethyl-tert.-butylamine; diamines, such as N,N-tetramethylethylenediamine; N,N-dimethylcyclohexylamine; bis-(2-hydroxy-ethyl)-cyclohexylamine; N-methyl-pyrrolidine, N-methyl-piperidine and N-methyl-morpholine; and amines substituted by further functional groups, such as N,N-dimethyl-aminoethanol and N,N-dimethylaminoneopentanol. Furthermore, araliphatic amines, such as tribenzylamine and N,N-dimethylbenzylamine, and polyamines with tertiary amino groups, such as triethylenediamine and bis-(2-dimethylaminoethyl)-methylamine can also be used; tetraalkylammonium hydroxides, for example tetraethylammonium hydroxide, can also be employed as the bases.

In general, the bases are used in the process according to the invention in an amount of 0.01 to 0.5 mol, preferably 0.05 to 0.3 mol, per mol of aldehyde of the formula (II). The pH value of the reaction solution should be 8 to 12, preferably 10 to 12.

In carrying out the process according to the invention, it can be advantageous to add inert organic solvents to the mixture of the aldehyde of the formula (II) and of the aqueous formaldehyde, in order to achieve a better solubility of the aldehyde of the formula (II) in the aqueous formaldehyde solution, or a homogeneous solution.

Inert organic solvents which can be used are the solvents which are known for this purpose, preferably lower aliphatic alcohols, such as methanol, ethanol, propanol and isopropanol, and aliphatic and alicyclic ethers, such as diethyl ether, tetrahydrofurane and dioxane.

The amount of solvent which is appropriately used depends on the nature of the acrylaldehyde of the formula (II) and can easily be appropriately determined by some preliminary experiments.

Furthermore, the reaction of the 2-alkylacrylaldehyde can also be carried out in the presence of weakly, moderately strongly or strongly basic ion exchangers or their mixtures. Suitable ion exchangers are listed in Houben-Weyl, Methoden der Organ. Chemie (Methods of Organic Chemistry), volume 1/1, page 529. Preferred ion exchangers which can be used are the strongly basic ion exchangers with tetraalkylammonium or trialkylhydroxyalkylammonium groups. The ion exchanger is preferably used in the commercially available granular form. If the reaction is carried out discontinuously, for example in a stirred vessel, the ion exchanger is used in an amount of about 10 to 80, preferably of 20 to 60, percent by volume, relative to the total reaction solution. It is also possible to use an exchanger column which is customary in the art and to pass the mixture of 2-alkylacrylaldehyde and aqueous formaldehyde solution through continuously. The abovementioned solvents can also be used here, appropriately as solubilising agents.

The reaction temperature to be maintained depends on the nature of the base, which serves as the condensing agent: if inorganic bases are used, for example the hydroxides of alkali metals and alkaline earth metals, the reaction temperature is about $-10°$ to 40° C., preferably $-10°$ to 10° C., particularly preferred $-5°$ to 5° C. When tert.-amines and basic ion exchangers are employed, the temperature range from about $-10°$ to 100° C., preferably 10° to 100° C., applies.

The process according to the invention can be carried out either discontinuously or continuously. In the discontinuous procedure, one can, for example, bring together acrylaldehydes of the formula (II), the formaldehyde solution and the base in the chosen ratio, and optionally the organic solvent, at the chosen temperature, whilst stirring, and to keep the reaction mixture at the reaction temperature for an appropriate time.

In general, reaction times of between 0.2 and 24 hours, preferably 0.5 to 12 hours, in particular of 5 to 12 hours, are required. The reaction time required in an individual case can be easily determined in the customary manner by following the course of the reaction using analytical methods or by a few preliminary experiments.

In general, the process according to the invention is carried out under normal pressure. However, one can also carry out the reaction under reduced or elevated pressure.

The 2,2-dimethylolalkanal obtained as the reaction product can subsequently be reduced in the customary manner to the trimethylolalkane, but it can be advantageous first to separate off the amine used as the base and the formaldehyde employed in excess, as well as any unreacted 2-alkylacrylaldehyde, for example, by subjecting the reaction mixture to incipient distillation in the pressure range between 0.5 and 8 bars.

The reduction of the 2,2-dimethylolalkanal obtained to the trimethylolalkane can be carried out in a manner which is in itself known. It can be carried out either with catalytically activated hydrogen or with nascent hydrogen. Furthermore, the 2,2-dimethylolalkanal can also be reduced with alkylaminoboranes and/or borohydrides of the alkali metals and alkaline earth metals.

The 2,2-dimethylolalkanal obtained in the process according to the invention is preferably reduced in the presence of a hydrogenation catalyst under an elevated pressure of hydrogen, for example according to GB-PS No. 1 919 792.

The trimethylolalkanes, for example trimethylolethane and trimethylolpropane, which can be prepared from 2,2-dimethylolalkanals are industrially important intermediate products for the preparation of plasticisers, lacquer raw materials, polyesters and polyurethanes. 2,2-Dimethylolalkanals are also needed for the preparation of dimethylolcarboxylic acids, for dyestuffs and for agents for combating pests (Ullmanns Enzyklopädie der techn. Chemie (Ullmann's Encyclopedia of Industrial Chemistry), volume 3, page 295 to 298).

The 2,2-dimethylolalkanes can be obtained in high yields, and without by-products, such as formates, being formed, by the process according to the invention using simple and easily accessible condensing agents. Hence, the process is particularly economic and does not pollute the environment.

The process according to the invention may be illustrated with the aid of the Examples which follow.

EXAMPLE 1

168 g (2 mols) of 2-ethylacrylaldehyde, 0.5 g of hydroquinone, 3,000 g of a 30% strength aqueous formaldehyde solution (30 mols) and 20 g (0.2 mol) of triethylamine were brought together and kept at the boiling point for half an hour. Thereafter, 2,031 g of the reaction liquid were distilled off. 0.07 mol of triethylamine was added to the distillate and the mixture was likewise kept at the reflux temperature for half an hour. The product thus obtained was partially evaporated and combined with the residue of the first distillation. On the basis of an analysis, the mixture (1,997 g) contained 12.1% of 2,2-dimethylolbutanal, which corresponds to a yield of 90.3%, relative to the 2-ethylacrylaldehyde employed.

EXAMPLE 2

140 g (2 mols) of 2-methylacrylaldehyde, 3,000 g of a 30% strength aqueous formaldehyde solution (30 mols), 0.5 g of hydroquinone and 20 g (0.2 mol) of triethylamine were kept at the boiling point for 30 minutes, using a reflux condenser. The reaction product was then subjected to incipient distillation, whereupon a residue of 910 g remained which, according to analysis, contained 23.3% by weight of 2,2-dimethylolethanal. This corresponds to a yield of 88.2%, relative to the 2-methylacrylaldehyde employed.

EXAMPLE 3

49 g (0.5 mol) of 2-propylacrylaldehyde and 500 g of a 30% strength aqueous formaldehyde solution (5 mols) were cooled to 0° C. 21 g of a 20% strength sodium hydroxide solution were then added dropwise, whilst stirring. The mixture was stirred at 1°-3° C. for 6 hours. Thereafter, the 2,2-dimethylolpentanal content was 9.7%. This corresponds to a yield of 74.6%, relative to the 0.5 mol of 2-propylacrylaldehyde employed.

EXAMPLE 4

42 g (0.5 mol) of 2-ethylacrylaldehyde and 600 g of a 30% strength aqueous formaldehyde solution (6 mols) together with 200 g of a commercially available strongly basic anion exchanger (poly-vinylbenzyltrimethylammonium hydroxide) were kept at 30° C. in a stirred vessel for 18 hours. The reaction liquid was then separated off from the anion exchanger and subjected to incipient distillation down to about one third. This distillate was brought together with the anion exchanger again for subsequent reaction and the mixture was stirred at 30° C. for 6 hours. The reaction product obtained was separated off from the anion exchanger, partially evaporated and combined with the residue of the first distillation, whereupon 539 g of product resulted which, according to analysis, contained 11.3% by weight of 2,2-dimethylolbutanal; this corresponds to a yield of 90.9%, relative to the 0.5 mol of 2-ethylacrylaldehyde employed.

EXAMPLE 5

49 g (0.5 mol) of 2-propylacrylaldehyde and 1,000 g of a 30% strength aqueous formaldehyde solution (10 mols) were cooled to 12° C. and 10 g (0.1 mol) of triethylamine were added, whilst stirring. The mixture was stirred for 11 hours and kept at 10°-13° C. The reaction product was then neutralised with formic acid and subjected to incipient distillation under normal pressure. A residue of 263 g remained which, according to analysis, contained 25.1% by weight of 2,2-dimethylolpentanal, corresponding to a yield of 89.2%, relative to the 2-propylacrylaldehyde employed.

What is claimed:

1. A process for the preparation of a 2,2-dimethylolalkanal of the formula

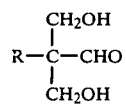

wherein R denotes an unsubstituted straight chain or branched alkyl radical with up to 15 carbon atoms or a $C_1$ to $C_4$ alkoxy substituted straight or branched alkyl radical with up to 15 carbon atoms,
which comprises contacting a 2-alkylacrylaldehyde of the formula

wherein R has the meaning indicated above, with formaldehyde in the presence of water and a hydroxide or carbonate of an alkali metal or alkaline earth metal, a tertiary amine or a basic ion exchanger employing a molar ratio of 2-alkylacrylaldehyde to formaldehyde of 1:8 to 1:30 and a temperature in the range of −10° C. to 100° C.

2. A process according to claim 1 where R is a straight or branched alkyl group with up to 15 carbon atoms.

3. A process according to claim 1 wherein said 2-alkylacrylaldehyde is select from the group consisting of methylacrylaldehyde, 2-ethylacrylaldehyde, 2-propylacrylaldehyde, and 2-butylacrylaldehyde.

4. A process according to claim 1 wherein 0.01 to 0.5 mol of base is used per mol of 2-acrylaldehyde.

5. A process according to claim 1 wherein the reaction of the acrylaldehyde with formaldehyde is carried out at a pH of the reaction solution in the range from 8 to 12.

6. A process according to claim 1 wherein the base is alkali metal hydroxide or alkaline earth metal hydroxide and the reaction is performed at the temperature in the range of −10° to +40° C.

7. A process according to claim 1 wherein the reaction is carried out in the presence of a tertiary amino at a temperature from 10° to 100° C.

8. A process according to claim 1 wherein the reaction is carried out in the presence of a basic ion exchanger at a temperature in the range of 10° to 100° C.

9. A process according to claim 1 wherein a hydroxide or carbonate of an alkali metal or alkaline earth metal is employed and said hydroxide or carbonate is sodium hydroxide, potassium hydroxide, calcium hydroxide, barium hydroxide, sodium carbonate or potassium carbonate.

10. A process according to claim 1 wherein a tertiary amine is employed and said tertiary amine is trimethylamine, tri-n-propylamine, triethylenediamine, tri-isopropylamine, tri-n-butylamine, triisobutylamine, tri-tert.-butylamine, methyldiisopropylamine, dimethyl-tert.-butylamine, N,N-tetramethyl-ethylenediamine, N,N-dimethylcyclohexylamine, bis-(2-hydroxy-ethyl)-cyclohexylamine, N-methyl-pyrrolidine, N-methyl-piperidine, M-methyl-morpholine, N,N-dimethylaminoethanol, N,N-dimethylaminoneopentanol, tribenzylamine, N,N-dimethylbenzylamine, triethylenediamine or bis-(2-dimethylaminoethyl)-methylamine.

11. A process according to claim 1 wherein a tertiary amine is employed which is a heterocyclic, aliphatic or cycloaliphatic amine with up to 20 carbon atoms.

* * * * *